(12) United States Patent
Shinoda et al.

(10) Patent No.: US 9,162,003 B2
(45) Date of Patent: Oct. 20, 2015

(54) AIR PURIFICATION DEVICE FOR VEHICLE

(75) Inventors: Yoshihisa Shinoda, Susono (JP);
Kazuhiro Sugimoto, Susono (JP);
Hiroaki Katsumata, Susono (JP)

(73) Assignee: TOYOTA JIDOSHA KABUSHIKI KAISHA, Toyota-Shi (JP)

( * ) Notice: Subject to any disclaimer, the term of this patent is extended or adjusted under 35 U.S.C. 154(b) by 0 days.

(21) Appl. No.: 14/394,554

(22) PCT Filed: Apr. 25, 2012

(86) PCT No.: PCT/JP2012/061021
§ 371 (c)(1),
(2), (4) Date: Oct. 15, 2014

(87) PCT Pub. No.: WO2013/161012
PCT Pub. Date: Oct. 31, 2013

(65) Prior Publication Data
US 2015/0050189 A1    Feb. 19, 2015

(51) Int. Cl.
*A61L 9/03*    (2006.01)
*B01D 53/86*    (2006.01)
*F28F 1/12*    (2006.01)

(52) U.S. Cl.
CPC .............. *A61L 9/03* (2013.01); *B01D 53/8675* (2013.01); *B01D 2253/102* (2013.01); *B01D 2255/1025* (2013.01); *B01D 2255/1026* (2013.01); *B01D 2255/2073* (2013.01); *B01D 2255/20738* (2013.01); *B01D 2255/20746* (2013.01); *B01D 2255/20753* (2013.01); *B01D 2255/20761* (2013.01); *B01D 2259/4558* (2013.01); *B01D 2259/4566* (2013.01); *F28F 1/128* (2013.01); *F28F 2245/00* (2013.01)

(58) Field of Classification Search
CPC ........................................................ A61L 9/03
USPC ........................................................ 422/121
See application file for complete search history.

(56) References Cited

U.S. PATENT DOCUMENTS

| | | | |
|---|---|---|---|
| 6,616,903 B2 * | 9/2003 | Poles et al. ..................... | 423/210 |
| 2003/0116021 A1 | 6/2003 | Oda et al. | |
| 2006/0182669 A1 | 8/2006 | Matumura et al. | |
| 2008/0256936 A1 * | 10/2008 | Zuberi ............................ | 60/299 |

FOREIGN PATENT DOCUMENTS

| | | |
|---|---|---|
| EP | 2689823 A1 | 1/2014 |
| JP | 2002-514966 A | 5/2002 |
| JP | 2006-231324 A | 9/2006 |
| JP | 2010-29816 A | 2/2010 |
| JP | 2010-201359 A | 9/2010 |
| JP | 2011-212639 A | 10/2011 |
| WO | 96/22146 A2 | 7/1996 |

* cited by examiner

*Primary Examiner* — Sean E Conley
(74) *Attorney, Agent, or Firm* — Kenyon & Kenyon LLP

(57) ABSTRACT

The invention relates to an air purification device for a vehicle and has an object to provide a DOR (Direct Ozone Reduction) system that can improve durability of activated carbon as an ozone purifier. FIG. 3 is a partially enlarged view of a fin of FIG. 2. FIG. 3(a) is a partial enlarged view of the fin in a front side, and FIG. 3(b) is a partially enlarged view of the fin in a rear side. As shown in FIGS. 3(a) and 3(b), in a louver, a coat amount of activated carbon is adjusted so as to gradually increase from a front side toward a rear side. Thereby, durability as the radiator can be improved, while oxidation degradation of the activated carbon by active oxygen is allowed to some degree.

7 Claims, 8 Drawing Sheets

AIR PURIFICATION DEVICE FOR VEHICLE

CROSS-REFERENCE TO RELATED APPLICATIONS

This is a national phase application based on the PCT International Patent Application No. PCT/JP2012/061021 filed Apr. 25, 2012, the entire contents of which are incorporated herein by reference.

TECHNICAL FIELD

The present invention relates to an air purification device for a vehicle, and relates to an air purification device for a vehicle that can purify ozone in the air.

BACKGROUND ART

Ozone that is a cause of generation of photochemical smog is generated by HC and NOx that are contained in exhaust gases of automobiles and plants causing photochemical reaction. Therefore, restraining the exhaust amounts of HC and NOx from automobiles is effective means for preventing occurrence of photochemical smog by restraining generation of ozone. Meanwhile, as the means for preventing generation of photochemical smog, it is also conceivable to purify ozone in the air directly. By not only aiming at reduction in the exhaust amounts of HC and NOx which are reactants, but also achieving purification of ozone that is a product, generation of photochemical smog can be prevented more effectively. From the viewpoint like this, in some areas including the state of California in the U.S.A., automobiles equipped with air purification devices for vehicles that can directly purify ozone in the air are in practical use. The air purification device for a vehicle is especially called a DOR (Direct Ozone Reduction) system.

As the DOR system as above, for example, Patent Literature 1 discloses the DOR system in which a metallic oxide such as manganese dioxide is supported by a vehicle component. The vehicle component is installed in the spot that is in contact with the air at a vehicle traveling time, and manganese dioxide has a function of purifying ozone contained in the air by converting the ozone into other substances such as oxygen. Consequently, according to the DOR system of Patent Literature 1, ozone in the air can be directly purified while the vehicle is traveling.

CITATION LIST

Patent Literature

Patent Literature 1: National Publication of International Patent Application No. 2002-514966
Patent Literature 2: Japanese Patent Laid-Open No. 2006-231324
Patent Literature 3: Japanese Patent Laid-Open No. 2011-212639

SUMMARY OF INVENTION

Problem to be Solved by the Invention

Incidentally, it is known that the function of purifying ozone is included in not only a metallic oxide such as manganese dioxide, but also activated carbon. Activated carbon is available at low cost, has ozone purification performance equivalent to a metallic oxide, and can purify ozone in a normal temperature (25° C.) range in addition. Therefore, activated carbon is regarded as promising as a substitute for a metallic oxide. However, when activated carbon is used as an ozone purifier, there arises the problem that the ozone purification function easily deteriorates.

In regard with the deterioration problem, the present inventors have already performed development focusing on the fact that active oxygen that is generated at the time of ozone decomposition of activated carbon is a main causative substance of the deterioration. Briefly introducing the development, though the details will be described later, active oxygen has an action of eliminating ozone purification sites of activated carbon, and the probability of the active oxygen contacting the ozone purification site becomes higher toward a rear part from a vehicle front part. Based on the knowledge as above, the present inventors develop an air purification device that can restrain deterioration of the ozone purification function of activated carbon caused by active oxygen by reducing the coat amount of activated carbon toward the rear part from the vehicle front part, in the vehicle component.

However, when the present inventors performed further development from the viewpoint of durability of activated carbon as an ozone purifier, instead of the viewpoint of deterioration of the ozone purification function of activated carbon, the possibility that a fear remains in durability is shown with coat amount adjustment based on the aforementioned contact probability.

The present invention is made in the light of the aforementioned problem. Namely, the present invention has an object to provide a DOR system that can improve durability of activated carbon as an ozone purifier.

Means for Solving the Problem

To achieve the above described object, a first aspect of the present invention is an air purification device for a vehicle, comprising:

a vehicle component comprising an air inflow port through which air flows in at a vehicle traveling time, an air exhaust port through which the air flowing in from the air inflow port is discharged to an outside, and an internal passage that connects the air inflow port and the air exhaust port; and an ozone purifier that is supported on a wall surface of the internal passage, and contains activated carbon, wherein a support amount of the ozone purifier is smaller at the air inflow port side than at the air exhaust port side.

A second aspect of the present invention is the air purification device for a vehicle according to the first aspect, wherein the vehicle component is a heat exchanger that performs heat exchange between inflow air and the wall surface, and the support amount of the ozone purifier that is supported in a predetermined region at the air inflow port side of the wall surface is zero.

A third aspect of the present invention is the air purification device for a vehicle according to the first or the second aspect, wherein the vehicle component is a radiator or an intercooler.

A fourth aspect of the present invention is the air purification device for a vehicle according to any one of the first to the third aspects, wherein the ozone purifier further contains at least one of manganese, iron, cobalt, nickel, copper, ruthenium, and rhodium.

Advantageous Effect of Invention

According to the knowledge which is newly obtained by the present inventors this time, it has become clear that the durability of the activated carbon can be improved more by increasing the coat amount of the activated carbon from the vehicle front part to the rear part than by decreasing the coat amount of the activated carbon from the vehicle front part to the rear part. Therefore, according to the first invention based on the present knowledge, the DOR system that can improve durability of the ozone purifier supported on the wall surface of the above described internal passage can be provided.

According to the second invention, the support amount of the ozone purifier supported in the above described predetermined region is made zero, and therefore, the inflow air can be brought into direct contact with the wall surface of the above described internal passage in the predetermined region. Therefore, the heat exchanging performance can be improved more compared with the case in which the ozone purifier is also supported in the predetermined region. Therefore, according to the present invention, in the case in which the vehicle component is a heat exchanger, the DOR system that can improve durability of the ozone purifier while ensuring the cooling performance thereof can be provided.

According to the third invention, the ozone purifier is provided in the radiator or the intercooler where engine cooling water or the like flows therein, and therefore, in the ozone purifier, an ozone purification reaction using heat of the engine cooling water or the like can be caused to proceed efficiently.

According to the fourth invention, at least one of manganese, iron, cobalt, nickel, copper, ruthenium and rhodium is combined with activated carbon, and can be supported on the wall surface of the above described internal passage as the above described ozone purifier.

DESCRIPTION OF EMBODIMENT

Figure 1:
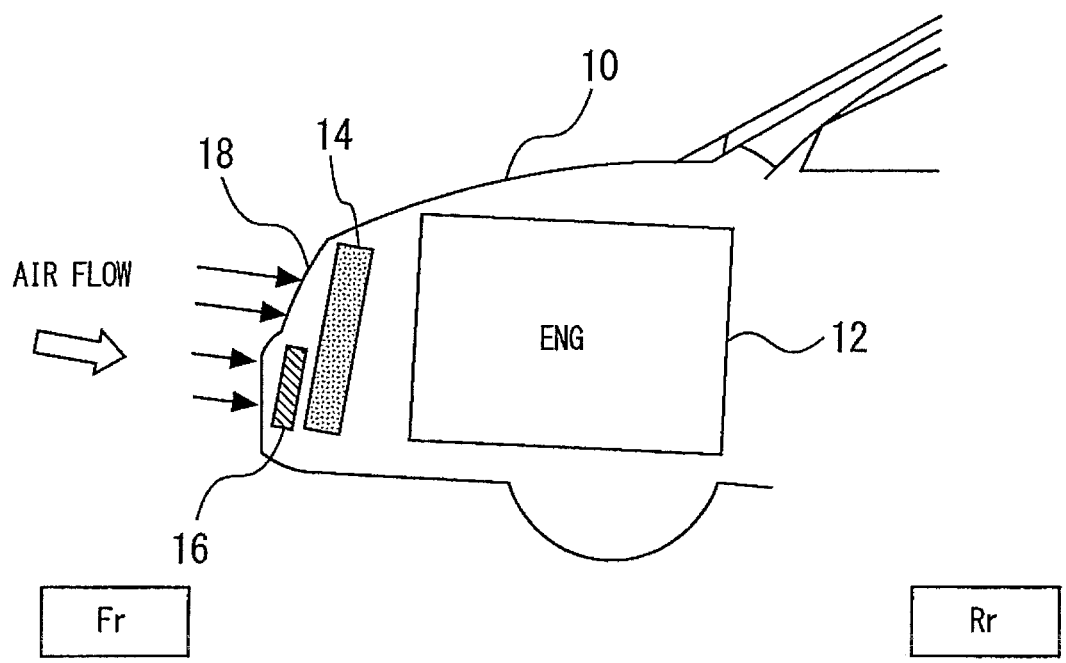
FIG. 1 is a schematic view showing a configuration of a vehicle loaded with an air purification device of the present embodiment.

Hereinafter, an embodiment of the present invention will be described with reference to FIG. 1 to FIG. 8. FIG. 1 is a schematic view showing a configuration of a vehicle loaded with an air purification device of the present embodiment. A vehicle 10 includes an internal combustion engine 12 as a power plant. An exhaust gas that is discharged from the internal combustion engine 12 contains HC and NOx. Ozone is generated by a photochemical reaction with HC and NOx as reactants. Therefore, the air purification device is loaded on the vehicle 10 including the internal combustion engine 12, and ozone in air is purified during travel of the vehicle 10, whereby an influence which the vehicle 10 has on the environment can be reduced.

In the vehicle 10, a radiator 14 that cools cooling water that is circulated to the internal combustion engine 12 is disposed in front of the internal combustion engine 12. A capacitor 16 for an air-conditioner is mounted in front of the radiator 14. As shown by the arrows in FIG. 1, at a time of travelling of the vehicle 10, air is taken in from a bumper grill 18 on a front surface of the vehicle 10, and the air which is taken in passes through the capacitor 16, and the radiator 14 in this sequence to be discharged rearward.

Figure 2:
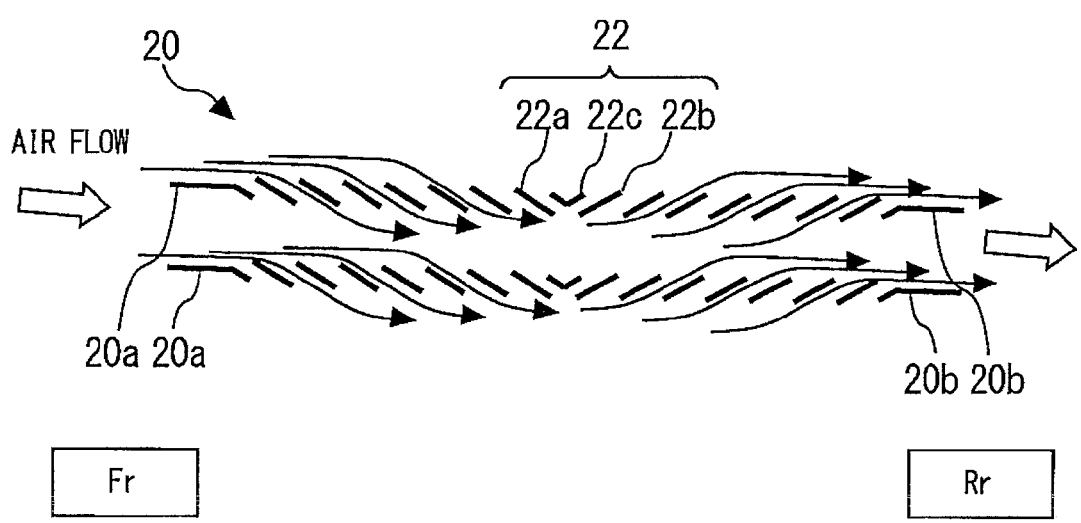
FIG. 2 is a view showing a sectional view of the radiator 14.

An aluminum fin equipped with louvers is included in a core of the radiator 14. FIG. 2 is a view showing a sectional view of the radiator 14. As shown in FIG. 2, in a fin 20 of the radiator 14, a plurality of louvers 22 are formed. The louver 22 is configured by inclined pieces 22a and 22b that are inclined diagonally with respect to flat portions 20a and 20b of the fin, and folded pieces 22c that are formed by folding. According to a configuration of the louver 22 like this, pressure loss can be generated when the air passes through the louvers 22, and therefore, a flow velocity thereof can be reduced. Further, a secondary flow of the air also can be generated. Therefore, heat radiation performance by the radiator 14 can be improved.

Figure 3:
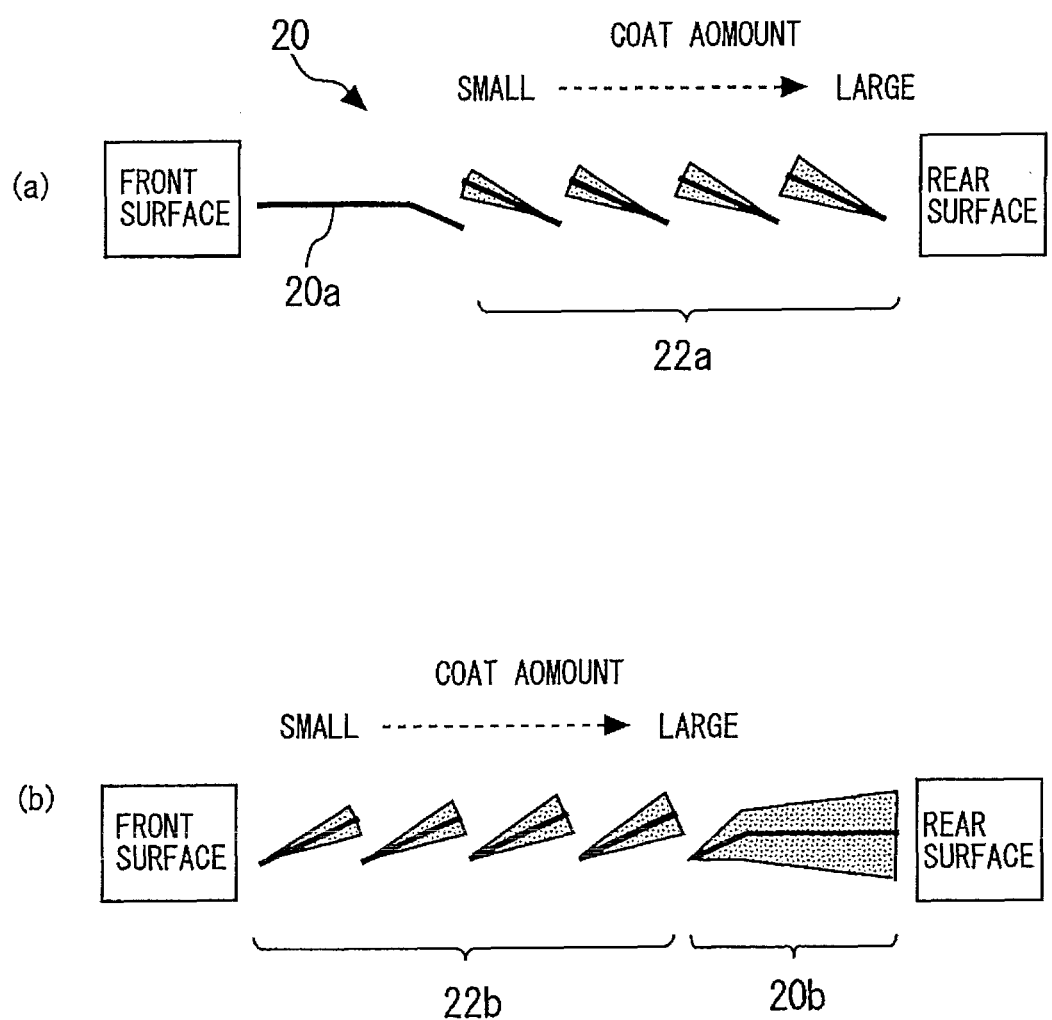
FIG. 3 is a partially enlarged view of the fin 20 in FIG. 2.

The air purification device of the present embodiment is formed by coating the fin 20 in FIG. 2 with activated carbon as an ozone purifier. FIG. 3 is a partially enlarged view of the fin 20 in FIG. 2. FIG. 3($a$) is a partially enlarged view of the fin 20 in a front side, and FIG. 3($b$) is a partially enlarged view of the fin 20 in a rear side. As shown in FIGS. 3($a$) and 3($b$), in the louver 22, a coat amount of activated carbon is adjusted so as to gradually increase from a front side toward a rear side. The reason why the coat amount is adjusted in such a manner will be described with reference to FIG. 4 to FIG. 6 concerning the knowledge that is already obtained by the present inventors, and FIG. 7 concerning knowledge that is newly obtained.

Figure 4:
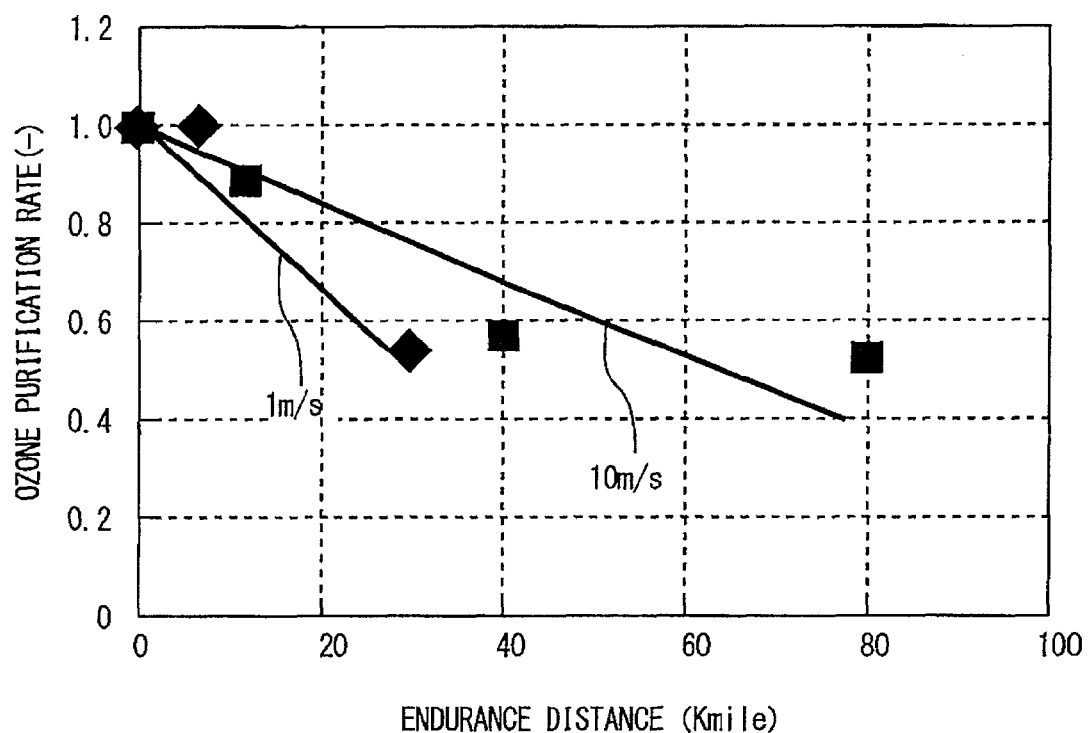
FIG. 4 is a diagram showing a result of an ozone purification test in a case of changing a passing velocity of an ozone-containing gas.

FIG. 4 is a diagram showing a result of an ozone purification test in a case of changing a passing velocity of an ozone-containing gas. The axis of abscissa of FIG. 4 represents an endurance distance (kilo mile), and an axis of ordinates represents a relative value with an ozone purification rate in an initial state (at a time of an endurance distance of zero kilo mile) as a reference, respectively. Respective data shown in FIG. 4 are obtained by measuring ozone concentrations at rear sides of activated carbons when the two activated carbons with equal sizes and specific surface areas are prepared, and the gas containing ozone with a fixed concentration is passed at different speeds (at a wind velocity of 1 m/s and a wind velocity of 10 m/s) toward the rear sides from front sides of the two activated carbons.

As shown in FIG. 4, the ozone purification rates of the activated carbons reduce more as the endurance distance becomes longer. Further, as shown in FIG. 4, a reduction degree of the ozone purification rate of the activated carbon changes in accordance with the velocity of the ozone-containing gas to be passes. More specifically, when the ozone-containing gas is passed at a wind velocity of 1 m/s, the ozone purification rate reduces to a half of the ozone purification rate in the initial state at approximately 30 kilo miles, whereas when the ozone-containing gas is passed at a wind velocity of 10 m/s, the ozone purification rate shows approximately 70% or more of the ozone purification rate in the initial state even at approximately 30 kilo miles, and the ozone purification rate finally reduces to approximately a half of the ozone purification rate in the initial state in a vicinity of approximately 60 kilo miles. Namely, when the ozone-containing gas is passed at a low velocity (a wind velocity of 1 m/s), the reduction degree of the ozone purification rate becomes larger as compared with the case of passing the ozone-containing gas at a high velocity (a wind velocity of 10 m/s).

Figure 5:
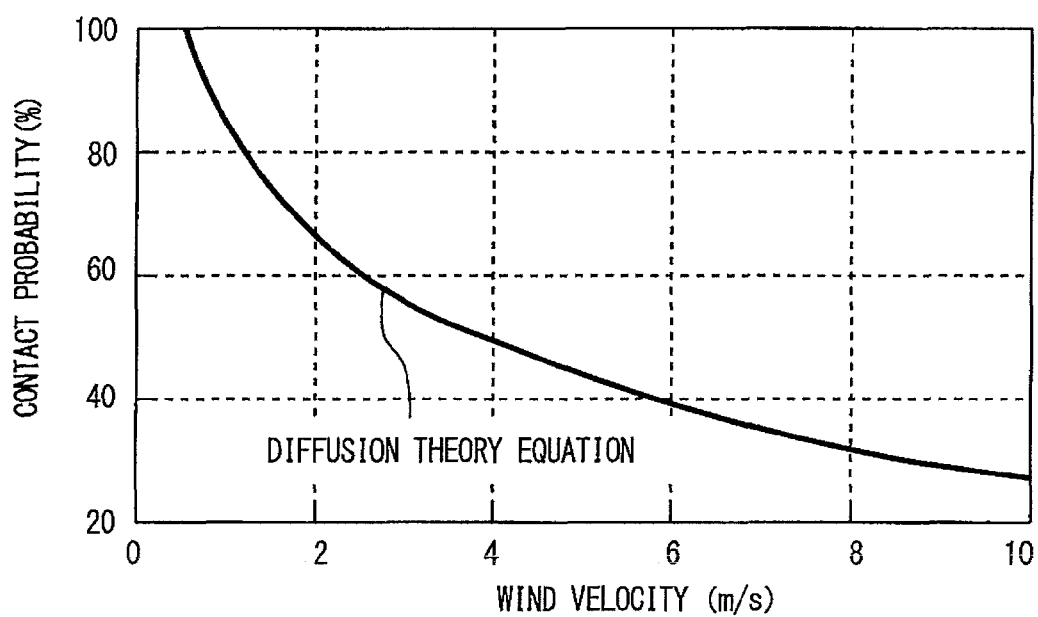
FIG. 5 is a diagram showing a relationship of a velocity of a gas that is passed through the radiator, and a probability of the gas contacting the radiator.

FIG. 5 is a diagram showing a relationship of a velocity of a gas that is passed through the radiator, and a probability of the gas contacting the radiator (hereinafter, called "a gas contact probability"). The graph is calculated by applying a diffusion theory equation of Gormley-Kennedy to a model of an aluminum honeycomb type radiator. As shown in FIG. 5, in a vicinity of a wind velocity of 1 m/s, the gas contact probability is approximately 100%, and in a vicinity of a wind velocity of 10 m/s, the gas contact probability is approximately 10%. Namely, the gas contact probability is high when the passing gas velocity is low, and gradually reduces as the passing gas velocity becomes higher.

From FIGS. 4 and 5, it is found out that there is a correlation between the reduction degree of the ozone purification rate, and the gas contact probability. Namely, from the graph of FIG. 5, it is known that as the passing gas velocity is lower, the gas contact probability becomes higher, and as the passing gas velocity is higher, the gas contact probability becomes lower. Further, from the graph in FIG. 4, it is known that as the passing velocity is lower, the reduction degree of the ozone purification rate becomes larger, and as the passing velocity is higher, the reduction degree of the ozone purification rate becomes smaller. Accordingly, from FIGS. 4 and 5, it is known that as the gas contact probability is higher, the reduction degree of the ozone purification rate becomes larger, and as the gas contact probability is lower, the reduction degree of the ozone purification rate becomes smaller.

Figure 6:
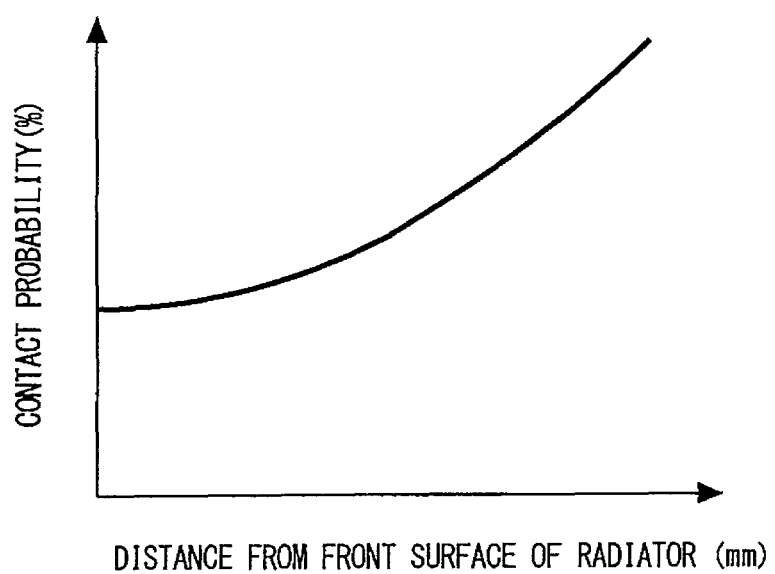
FIG. 6 is a diagram showing a relationship of a distance from a front surface of the radiator 14, and the gas contact probability.

Further, FIG. 6 is a diagram showing a relationship of a distance from a front surface of the radiator 14, and the gas contact probability. As shown in FIG. 6, as the distance from the front surface of the radiator 14 is longer, the gas contact probability increases more. The reason thereof is that as described at the time of explanation of FIG. 2, in the radiator 14, the louvers 22 are formed, whereby the air flow can be decelerated, or the secondary flow thereof can be generated. Accordingly, from FIG. 4 to FIG. 6, it is known that as the distance from the front surface of the radiator 14 is longer, the gas contact probability becomes higher, and the reduction degree of the ozone purification rate becomes larger.

Here, the present inventors already perform development that focuses on the fact that reduction in the ozone purification rate of activated carbon is mainly caused by oxidizing action by active oxygen that is generated at a time of ozone decomposition of the activated carbon. Namely, if active oxygen is generated during travel of the vehicle, the active oxygen flows to the rear side from the front side. The present inventors infer that the probability of active oxygen contacting the radiator is higher toward the rear side and therefore, elimination of the activated carbon becomes more remarkable toward the rear side, and develop the radiator in which an activated carbon coat amount is reduced from the front side to the rear side.

Figure 7:
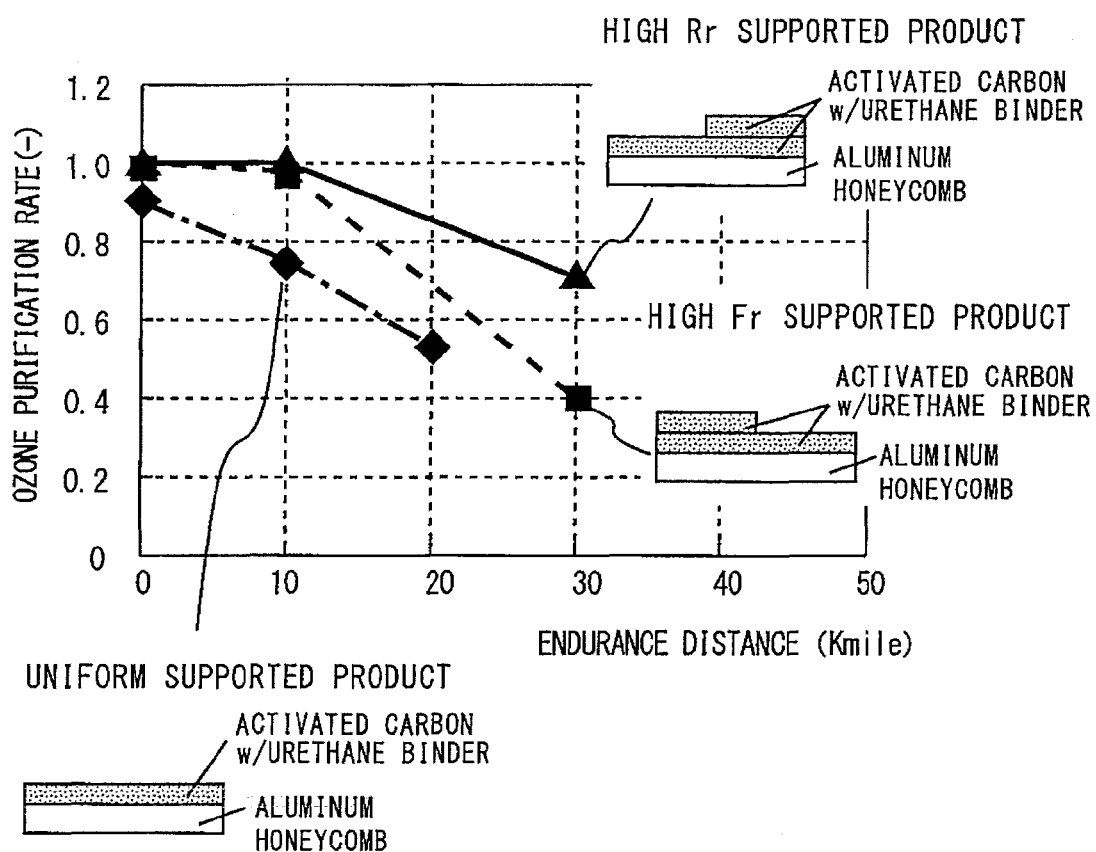
FIG. 7 is data showing a result of the endurance test.

However, according to the durability test by the present inventors, the data exactly opposite to the above described inference was obtained. FIG. 7 is data showing a result of the endurance test. Three kinds of data shown in FIG. 7 respectively show a high Rr supported product (a solid line), a high Fr supported product (a broken line) and a uniform supported product (an alternate long and short dash line). Note that as schematically shown in FIG. 7, the high Rr supported product is a product in which an activated carbon coat amount at the rear side is adjusted to be larger as compared with the front side. Further, the high Fr supported product is a product in which an activated carbon coat amount at the front side is adjusted to be larger as compared with the rear side. Further, the uniform supported product is a product in which a difference is not provided in the activated carbon coat amount from the front side to the rear side.

An axis of abscissa of FIG. 7 represents an endurance distance (kilo mile), and an axis of ordinates represents a relative value with the ozone purification rate in the initial state (at the time of an endurance distance of zero kilo mile) of the high Fr supported product, as a reference respectively. As shown in FIG. 7, the ozone purification rate of activated carbon reduces in accordance with the endurance distance, and the reduction degree differs in accordance with the activated carbon coat amount. Namely, the reduction degrees in the high Rr supported product and the high Fr supported product are smaller as compared with the reduction degree of the uniform supported product. Further, the reduction degree in the high Rr supported product is smaller as compared with the reduction degree of the high Fr supported product.

As the reasons why the data shown in FIG. 7 is obtained are as follows: it is considered that even when the activated carbon is deteriorated by the oxidizing action by active oxygen, the specific area of the activated carbon can remain to some degree. Further, it is considered that if the specific surface area of the activated carbon remains to some degree, in the rear side where the gas contact probability is high, the possibility of being capable of positively decomposing ozone becomes high correspondingly. Based on the inference as above, in the present embodiment, the coat amount of the activated carbon with which the fin 20 is coated is adjusted.

Figure 8:
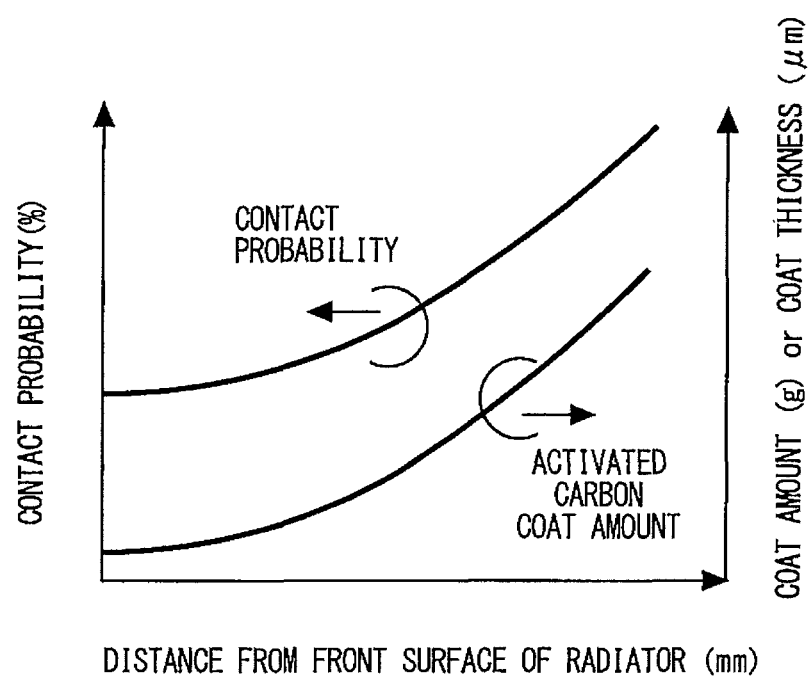
FIG. 8 is a diagram showing a specific example of the coat amount of the activated carbon with which the fin 20 is coated.

FIG. 8 is a diagram showing a specific example of the coat amount of the activated carbon with which the fin 20 is coated. As described on the occasion of explanation of FIG. 6, the gas contact probability increases in a quadratic function manner as the distance from the front surface of the radiator 14 becomes larger. Therefore, the coat amount of the activated carbon is increased in a manner of a logarithmic function or a proportional function in accordance with the distance from the front surface of the radiator 14, as shown in FIG. 8. Namely, the activated carbon coat amount is adjusted to be exactly opposite to the radiator which the present inventors developed before. Note that adjustment may be performed by a coat thickness of the activated carbon, instead of the coat amount of the activated carbon.

Returning to FIG. 3 again, explanation of the air purification device of the present embodiment will be continued. As shown in FIG. 3(a), the flat portion 20a is not coated with the activated carbon at all. By providing such an activated carbon uncoated spot, a fixed amount of the area of the surface where the air directly contacts the fin 20 can be ensured, on a front surface side of the radiator 14. Therefore, the original cooling function of the radiator 14 also can be ensured.

As above, according to the air purification device of the present embodiment, the activated carbon coat amount is adjusted to be increased from the front surface side to the rear surface side of the radiator 14, and therefore, the durability as the radiator 14 can be improved while the oxidation degradation of the activated carbon by active oxygen is allowed to some degree. Further, the activated carbon uncoated spot is provided at the flat portion 20a, and therefore, the original cooling function of the radiator 14 can be ensured.

Incidentally, while in the present embodiment, the radiator 14 is illustrated as the vehicle component, the present invention also can be applied to the intercooler. The intercooler is provided at a spot where a passage of the air is formed while the vehicle is traveling, and therefore, when activated carbon with a coat amount thereof adjusted similarly to the present embodiment is provided at the fin of the intercooler, the similar effect to the effect of the present embodiment can be obtained.

Further, while in the present embodiment, the radiator 14 including the fin 20 is used, the fin 20 is not always necessary. Namely, in place of the radiator 14, a so-called honeycomb radiator in which the cooling cores with fine passages being formed are densely packed may be used. In the case of using the honeycomb radiator, passage wall surfaces thereof are coated with activated carbon. Therefore, the pressure loss of the air flowing in the passage increases more toward the downstream side, and the flow velocity thereof reduces. Accordingly, the gas contact probability becomes larger toward the downstream side, and therefore, if the coat amount of activated carbon is adjusted similarly to the present embodiment, the effect as described above can be obtained.

Further, while in the present embodiment, the fin 20 is coated with activated carbon, the fin 20 may be coated with a single metal such as manganese, iron, cobalt, nickel, copper, ruthenium or rhodium, simultaneously with the activated carbon. Note that two kinds or more of these single metals may be coated at the same time.

DESCRIPTION OF REFERENCE NUMERALS

10 vehicle
12 internal combustion engine
14 radiator
16 capacitor
18 bumper grill
20 fin
20*a*, 20*b* flat portion
22 louvers
22*a*, 22*b* inclined pieces
22*c* folded pieces

The invention claimed is:

1. An air purification device for a vehicle, comprising:
a vehicle component comprising an air inflow port through which air flows in at a vehicle traveling time, an air exhaust port through which the air flowing in from the air inflow port is discharged to an outside, and an internal passage that connects the air inflow port and the air exhaust port; and
an ozone purifier that is supported on a wall surface of the internal passage, and contains activated carbon,
wherein a support amount of the ozone purifier is smaller at the air inflow port side than at the air exhaust port side.

2. The air purification device for a vehicle according to claim 1,
wherein the vehicle component is a heat exchanger that performs heat exchange between inflow air and the wall surface, and
the support amount of the ozone purifier that is supported in a predetermined region at the air inflow port side of the wall surface is zero.

3. The air purification device for a vehicle according to claim 1,
wherein the vehicle component is a radiator or an intercooler.

4. The air purification device for a vehicle according to claim 1,
wherein the ozone purifier further contains at least one of manganese, iron, cobalt, nickel, copper, ruthenium, and rhodium.

5. The air purification device for a vehicle according to claim 1,
wherein the activated carbon has a function of purifying ozone.

6. The air purification device for a vehicle according to claim 1,
wherein support amount of the activated carbon is smaller at the air inflow port side than at the air exhaust port side.

7. The air purification device for a vehicle according to claim 1,
wherein the air inflow port is positioned in the front side of the vehicle and the air exhaust port is positioned in the rear side of the vehicle.

* * * * *